(12) United States Patent
Xin et al.

(10) Patent No.: US 10,959,667 B2
(45) Date of Patent: Mar. 30, 2021

(54) INTELLIGENT SLEEP SYSTEM, AND USER SIDE SYSTEM AND CLOUD SIDE SYSTEM THEREOF

(71) Applicant: Moonmark Smart Technology (Shanghai) Co., Ltd., Shanghai (CN)

(72) Inventors: Zhiyu Xin, Shanghai (CN); Liqun Zhang, Shanghai (CN)

(73) Assignee: MOONMARK SMART TECHNOLOGY (SHANGHAI) CO., LTD., Shanghai (CN)

( * ) Notice: Subject to any disclaimer, the term of this patent is extended or adjusted under 35 U.S.C. 154(b) by 634 days.

(21) Appl. No.: 15/737,035

(22) PCT Filed: Jan. 14, 2015

(86) PCT No.: PCT/CN2015/070707
§ 371 (c)(1),
(2) Date: Dec. 15, 2017

(87) PCT Pub. No.: WO2015/106689
PCT Pub. Date: Jul. 23, 2015

(65) Prior Publication Data
US 2019/0069838 A1 Mar. 7, 2019

(30) Foreign Application Priority Data

Jan. 20, 2014 (CN) .......................... 201410025534.X

(51) Int. Cl.
*G16H 15/00* (2018.01)
*A61B 5/00* (2006.01)
(Continued)

(52) U.S. Cl.
CPC .......... *A61B 5/4815* (2013.01); *A61B 5/4806* (2013.01); *A61B 5/4809* (2013.01);
(Continued)

(58) Field of Classification Search
CPC ... A61B 5/4815; A61B 5/4806; A61B 5/4809; A61B 5/0002; A61B 5/024;
(Continued)

(56) References Cited

U.S. PATENT DOCUMENTS 9,438,044 B2 * 9/2016 Proud ..................... H02J 50/12
9,474,876 B1 * 10/2016 Kahn ................... A61B 5/4812
(Continued)

FOREIGN PATENT DOCUMENTS

CN 101697935 A 4/2010
CN 101954143 A 1/2011
(Continued)

OTHER PUBLICATIONS

Written Opinion issued by International Bureau on Apr. 28, 2015 for International Application PCT/CN2015/070707.
(Continued)

*Primary Examiner* — Kandasamy Thangavelu
(74) *Attorney, Agent, or Firm* — Finnegan, Henderson, Farabow, Garrett & Dunner, LLP

(57) ABSTRACT

Disclosed herein are an intelligent sleep system, and a client system and a cloud system thereof, wherein the client system comprises a multi-dimensional data acquisition module (101), a local data processing module (102), a client system communication module (103), and a driving execution module (104); and the cloud system comprises a cloud side communication module (201), a data management module (202), and a data mining module (203).

10 Claims, 2 Drawing Sheets

(51) Int. Cl.
  *H04L 29/08* (2006.01)
  *G16H 40/40* (2018.01)
  *G16H 40/67* (2018.01)
  *A61M 21/02* (2006.01)
  *G16H 50/70* (2018.01)
  *G06K 9/00* (2006.01)

(52) U.S. Cl.
  CPC ......... *A61M 21/02* (2013.01); *G06K 9/00523* (2013.01); *G16H 15/00* (2018.01); *G16H 40/40* (2018.01); *G16H 40/67* (2018.01); *G16H 50/70* (2018.01); *H04L 67/12* (2013.01)

(58) Field of Classification Search
  CPC .... A61B 5/4812; A61B 5/6819; G16H 40/40; G16H 15/00; G16H 40/67; G16H 50/70; A61M 21/02; G06K 9/00523; H04L 67/12; A47C 21/003; A47C 27/10; G06F 1/3206; H02J 50/01
  See application file for complete search history.

(56) References Cited

U.S. PATENT DOCUMENTS

| | | | | |
|---|---|---|---|---|
| 2006/0173257 A1* | 8/2006 | Nagai | ............... | A61B 5/6819 600/323 |
| 2012/0139722 A1 | 6/2012 | Wong et al. | | |
| 2012/0296156 A1* | 11/2012 | Auphan | ............... | A47C 21/003 600/28 |
| 2013/0072765 A1* | 3/2013 | Kahn | ............... | G06F 1/3206 600/301 |
| 2013/0234823 A1* | 9/2013 | Kahn | ............... | A61B 5/024 340/3.1 |
| 2013/0245389 A1* | 9/2013 | Schultz | ............... | A61B 5/0002 600/301 |
| 2014/0041127 A1* | 2/2014 | Codos | ............... | A47C 27/10 5/713 |

FOREIGN PATENT DOCUMENTS

| | | | | | |
|---|---|---|---|---|---|
| CN | 102043385 | | * | 5/2011 | ............ A61B 5/024 |
| CN | 102224503 | A | | 10/2011 | |
| CN | 102461135 | A | * | 5/2012 | ............ A61B 5/024 |
| CN | 102499806 | A | | 6/2012 | |
| CN | 202654115 | U | | 1/2013 | |
| CN | 103136629 | A | | 6/2013 | |
| CN | 203087145 | U | * | 7/2013 | ............ A61B 5/024 |
| CN | 13300819 | | * | 9/2013 | ............ A61B 5/024 |
| CN | 103330413 | A | | 10/2013 | |
| CN | 103431846 | A | | 12/2013 | |
| CN | 103780691 | A | | 5/2014 | |
| CN | 103780961 | A | | 5/2014 | |
| CN | 203838535 | U | | 9/2014 | |
| EP | 2 278 508 | A1 | * | 1/2011 | ............ G06F 19/00 |
| WO | WO 2009/102361 | A1 | * | 8/2009 | ............ A47C 27/08 |
| WO | WO 2013/1773380 | A2 | * | 11/2013 | ............ G06Q 50/22 |

OTHER PUBLICATIONS

International Search Report issued by International Bureau on Apr. 28, 2015 for International Application PCT/CN2015/070707.

* cited by examiner

INTELLIGENT SLEEP SYSTEM, AND USER SIDE SYSTEM AND CLOUD SIDE SYSTEM THEREOF

CROSS REFERENCE TO RELATED APPLICATION

The present application is a national stage entry of International Application No. PCT/CN2015/070707, filed Jan. 14, 2015, which is based on and claims the benefits of priority to Chinese Application No. 201410025534.X, filed Jan. 20, 2014, both of which are incorporated herein in their entireties.

TECHNICAL FIELD

The present invention is related to sleep systems, and in particular, to an intelligent sleep system, a client system, and a cloud system thereof.

TECHNICAL BACKGROUND

With the further development of Internet technology and the rapid development of Internet of Things technology and its applications, it has become possible for traditional products to bring high-quality user experience by introducing new technologies. A sleep support system that has the most stable and long-term cooperative relationship with people and has an important influence on users' physiology and psychology, the traditional framework and functional definitions of the sleep support system can no longer meet people's new requirements for sleep quality. There has been a linear decrease in the quality of sleep support for users over the life of a factory-styled spring and foam mattress. One of the reasons for this is due to elastic fatigue caused by the long-term work and changes in users' physical signs and psychological factors (growth, illness, critical events, or aging) over an average 5-8 year product life cycle that have required a change in form, content, and quality to the sleep support provided by the mattress. Nevertheless, the current dominant spring and foam mattress system cannot provide such change.

At the same time, users generate a large amount of data of sleep behavior and environment etc. everyday during sleep. These multidimensional data are of great significance to perceiving and improving the quality of sleep and health of the user. However, due to the complex factors such as being multidimensional, wide-area, and cross-over of these data, simple logic data operation processing models that rely solely on sensors and embedded processors do not have a comprehensive and accurate understanding, prediction and wisdom adaption at the practical level to users' demand for sleep quality and health. In fact, due to the complexity and specificity of the personalized sleep experience, it is even difficult for the users themselves to rely solely on the body experience to accurately sense and describe whether a product truly meets their demand for sleep quality and health.

SUMMARY OF THE INVENTION

In view of the defects in conventional technologies, the present invention aims to provide an intelligent sleep system and its client system and cloud system. The intelligent sleep system uses a combination of software and hardware and the cloud computing data mining techniques and modules to provide user-oriented intelligence sleep products services and other derived products and services by collecting, processing, sending, managing, mining, predicting, pushing, interacting and applying various user sleep data.

The client system of the intelligent sleep system according to the present invention includes a multidimensional data collection module 101, a local data processing module 102, a client system communication module 103 and a driver execution module 104;

Multi-dimensional data acquisition module 101 is used to collect human-machine environment information associated with the sleep activity of users of the client system through the non-intrusive multi-mode sensor cluster, and send the human-machine environment information to local data processing module 102, wherein the human-machine environment information includes the user's sleep behavior data and sleep environment data;

Local data processing module 102 is used to pre-process and then send the human-machine environment information to cloud system 2 corresponding to client system 1, and write the driver data received from cloud system 2 into driver program module 104 by a firmware, so as to optimally support the user's sleep activity at this stage and help the user obtain optimized sleep quality;

Client system communication module 103 is used for the data wireless transmission between client system 1 and cloud system 2;

Driver execution module 104 is used to execute a supporting action according to the driver data and the human-machine environment information.

Preferably, one or more of the following devices are further included:

A user experience evaluation measurement module 105 is configured to obtain the user's subjective attitude measurement data of sleep quality (based on the attitude metric) by using the support of an application (APP) in the intelligent terminal, and correlate the sleep quality subjective attitude measurement data with the corresponding sleep behavior data (acquired through multi-modal/channel sensor collecting) and sent the data to cloud system 2 after assigning timestamps;

Human-machine conversation module 106 is configured to measure the subjective attitude of the user's sleep quality to generate the sleep attitude data, and correlate the sleep attitude data with the corresponding sleep behavior data.

Preferably, driver execution module 104 sends the behavioral and electromechanical fatigue data of the included support units to local data processing module 102. Local data processing module 102 performs unit performance evaluations of the behavioral and electromechanical fatigue data and sends the performance evaluation data of the support unit to cloud system 2.

The cloud system of the intelligent sleep system provided by the present invention includes: a cloud communication module 201, a data management module 202, and a data mining module 203;

Cloud communication module 201 is used for the data wireless transmission between cloud system 2 and corresponding client system 1 in the cloud;

Data management module 202 is configured to, by means of cloud platform data mining, obtain a multi-dimensional user sleep behavior data set according to the widely distributed multivariate multi-channel man-machine environment information data collected by each client system 1, in order to support the data mining module 203 to obtain the node user sleep mode corresponding to each client system 1 and the user sleep behavior statistics corresponding to all the client systems;

Data mining module 203 is used to analyze the user sleep behavior data set by using a pattern recognition mode, in order to obtain the global user sleep mode of the global user and the user sleep mode of the node corresponding to each client system 1, to obtain the sleep feature knowledge of the global user and the user of the single client system, and to establish a mathematical model of a global user sleep mode and a node user sleep movie, and then generate a mode driver data packet of client system driver execution module 104 according to the global user sleep mode and the node user sleep, and send the driver data packet to client system 1.

Preferably, it also includes a sleep quality evaluation summary analysis module 204, wherein sleep quality evaluation summary analysis module 204 is configured to obtain the significant relationship between the sleep quality of the user at different levels and the parameters of driver execution module 104 by analyzing the user sleep behavior data set, such as the user's high-quality sleep mode parameter conditions of the node. And sleep quality evaluation summary analysis module 204 is configured to generate an optimized driver data packet that matches the high-quality sleep mode of each client system user based on a certain amount of data collection. The optimized driver data packet is used to drive driver execution module 104 so as to guide the user to achieve optimal sleep quality through interactive adjustment during user sleep.

Preferably, the analysis of the user sleep behavior data set specifically includes: performing a reflection layer attitude measurement on the sleep quality of the sleep activity that occurs during the valid period of the user, and the obtained measurement data will be the new data content in data management module 202, and obtaining the correlation between sleep feature knowledge and sleep quality by comparing with the existing precipitation data to generate a weighted sleep quality assessment.

Preferably, one or more of the following devices are further included:

A client system performance detection module 205 is used to monitor the performance of the support unit according to the performance evaluation data received from the support unit of client system 1;

A customized sleep data packet 206 is used to generate customized sleep data packet used as client system driver firmware.

Preferably, the user sleep behavior data set includes physical data of the time-based user sleep activity collected by client system 1 and its corresponding physiological indicator data and environmental indicator data.

Preferably, sleep quality evaluation summary analysis module 204 adjusts the optimized driver data packet according to the change of the parameter values in the user sleep behavior data set over time.

The intelligent sleep system provided by the present invention includes the above-mentioned client system 1 and the above-mentioned cloud system 2, and the wireless connection between the client system 1 and the cloud system 2.

Those skilled in the art shall understand that the intelligent sleep system can be applied to products such as sleeping pillows, seats, cushions and the like in the field of intelligent adjustment of human body contact environment in addition to being applied to mattresses.

Compared with conventional technologies, the invention has the following beneficial effects:

The invention can automatically adapt to the user's sleep behavior and posture, and give the support system the ability to meet the changing needs of the user's long-term sleep pattern through the knowledge discovery of long-term sleep behavior. Further, the technical problems that can be solved by applying the invention include:

1—Sleep behavior perception and capture. It can be composed of a sleep behavior awareness matrix unit and a semantic capture logic operation module for collecting the physical indicator data of the client sleep support system in the working state and the users' physiological indicator data associated with the sleep behavior, and sleep environmental indicator data (such as temperature and humidity, ambient illumination, noise, etc.). In addition, data collected by the client through support systems based on smartphone applications is also collected for alignment with the initial state of the system. The data is temporarily stored locally and sent to the cloud management platform via the Internet, thereby becoming the original data source for data mining and customized sleep knowledge production and application.

2—Provide an extendable sleep data cloud management platform, i.e., the cloud system. The cloud platform is used to manage the lifecycle data of the client node system, to support the user sleep behavior data management of all client node systems and to realize the remote monitoring of the system status and service task generation.

3—Sleep data mining system. The data involved in this system include the UGC data on the client side and the DGC data, which support the discovery and diachronic comparison of sleep patterns of the node system, the discovery and semantic analysis of abnormal sleep behaviors, and the user classification based on sleep patterns, the clustering, association and prediction. They also support the discovery and marketing decision-making of new product attributes based on type users, and support the discovery of new product opportunities and marketing knowledge in the related area.

4—Sleep support system remote status management system. It supports remote monitoring of the status of the client node system including the health status of each job unit in the node system, unit work loss, job unit-subsystem-system maintenance task demand forecast, and generation of maintenance service task list and service tasks.

5—Sleep support system client customized service list management. Based on the analysis of the node users and types of users by the sleep data mining system, it generates, for user nodes, the push and download service for the customized data packet (including the customized firmware) of the optimized sleep support system, and the push service of the health sleep guide and the sleep counseling and the like, as well as customized derived products for sleep aids (customized pillows, customized lumbar pads, etc.) outside the system.

6—B2B data products services. Designed for packet-based services in sleep-related healthcare and medical areas or other non-sleep products areas, it provides secondary mining and custom data services for healthcare and medical areas based on analysis of node users and types of users by the sleep data mining system.

BRIEF DESCRIPTION OF THE DRAWINGS

Other features, objects, and advantages of the invention will become more apparent by reading and referring the detailed description of the non-limiting embodiments by the following drawings, in which.

DETAILED DESCRIPTION OF EMBODIMENTS

The invention will be described in detail below with reference to specific embodiments. The following embodiments will help those killed in the art to further understand the invention, but not to limit the invention in any form. It should be noted that those killed in the art can make many variations and improvements without departing from the concept of the invention. These all belong to the protection scope of the invention.

Figure 1:
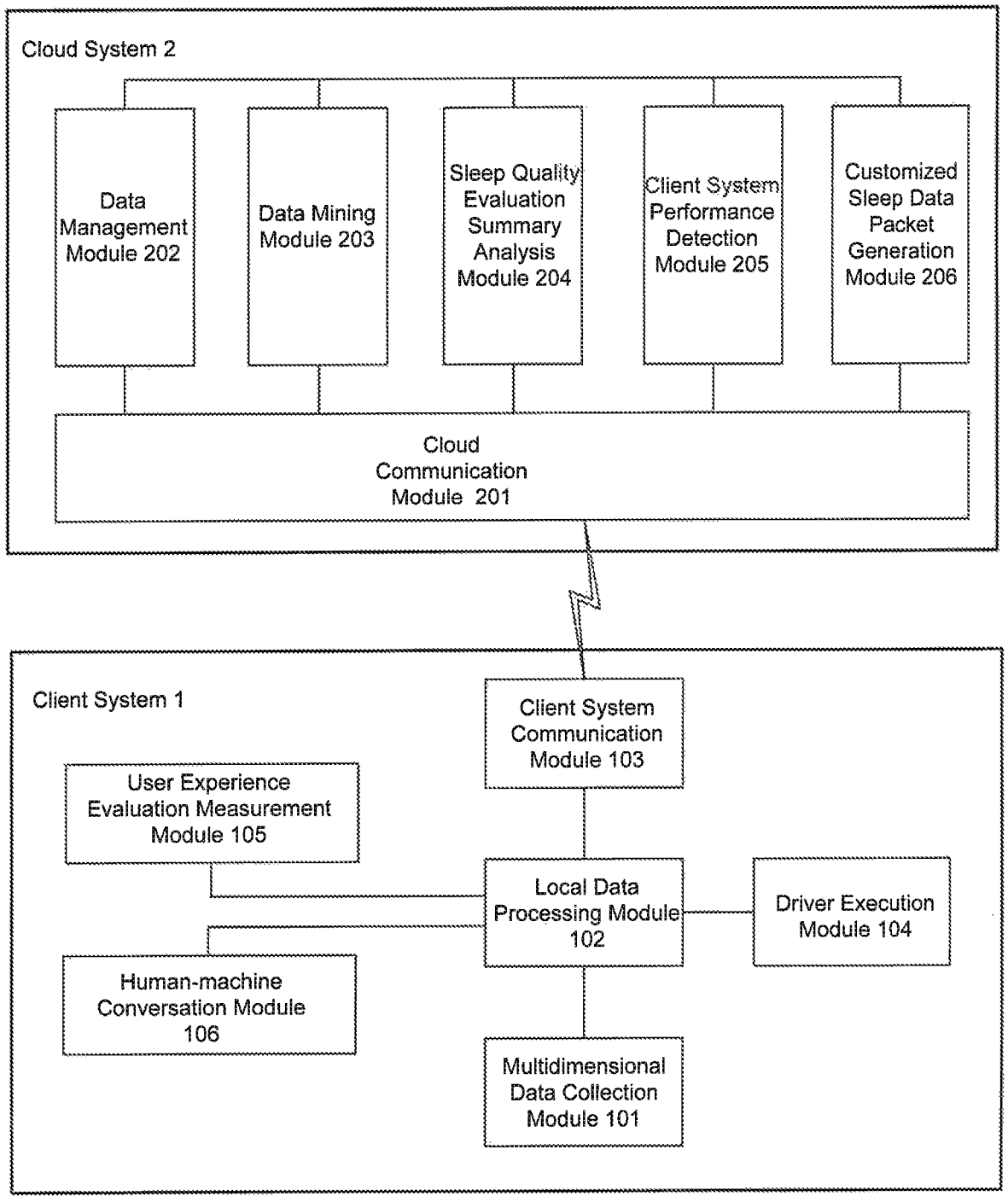
FIG. 1 is a structural diagram of the invention.
Figure 2:
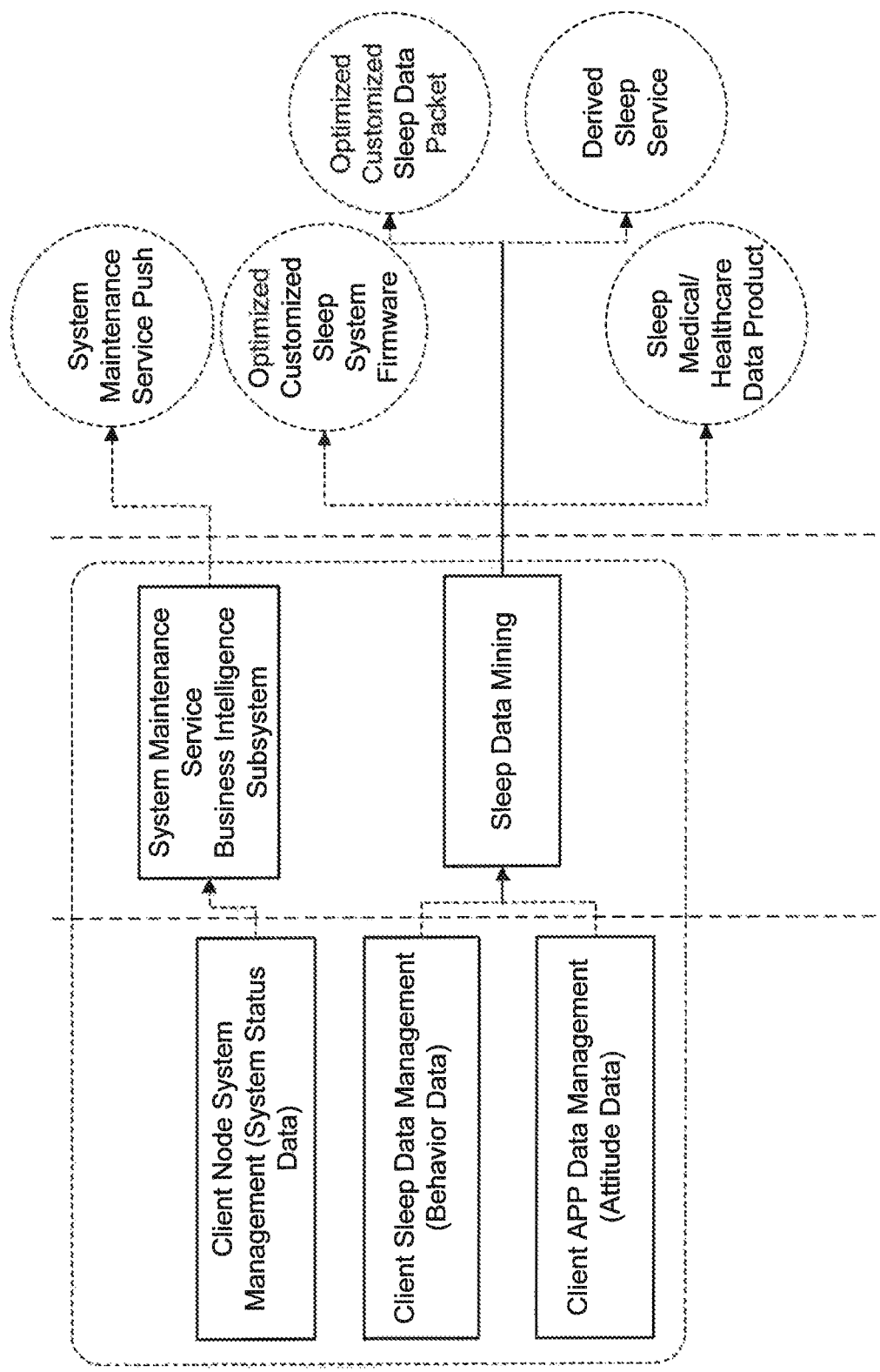
FIG. 2 is a schematic diagram of the invention.

As shown in FIG. 1, the intelligent sleep system provided by the invention includes a client system 1 and a cloud system 2, and the wireless connection between client system 1 and cloud system 2.

Client system 1 of the intelligent sleep system includes a multidimensional data collection module 101, a local data processing module 102, a client system communication module 103, a driver execution module 104, a user experience evaluation measurement module 105, and a human-machine conversation module 106. Client system 1, as a client node system, is mainly used to provide operation and status data—time-sequences system hardware and software running data to cloud platform 2. And the client system helps the platform discover the hidden troubles of the node system through alignment with the aging data of the system, so as to provide the original data for system maintenance and service push that are based on the business intelligence.

Multi-dimensional data collection module 101 is configured to collect the human-machine environment information associated with the sleep activity of the client system users by using the non-invasive multi-modal sensor cluster, and send the human-machine environment information to local data processing module 102. The human-machine environment information includes the user's sleep behavior data and sleep environment data. Non-intrusive multi-modal sensor clusters can mainly include sleep-behavior sensors embedded in comfort sensing layers in a form of a matrix of M×N, so as to obtain real-time and time-lapse sleep behavior data of users under system support. The real-time and time-lapse sleep behavior data will be used as input for local data processing module 102 inside client system 1 of this system. The specific human-machine environment information may include physical indicator data generated by the user sleep activity, user physiological indicator data based on the same time sequences and environmental indicator data (such as ambient temperature and humidity, ambient light attribute data, etc.).

Local data processing module 102 is configured to preprocess and then send the human-machine environment information to cloud system 2 corresponding to client system 1, and write the driver data received from cloud system 2 into driver program module 104 by a firmware, so as to provide best support to the user's sleep activity at this stage to assist the user in obtaining optimized sleep quality and also to receive subjective attitude measurement data (e.g., evaluation data input by an application of the intelligent terminal) on sleep quality from a user of user experience evaluation measurement module 105.

Client system communication module 103 is used for wireless transmission of data between client system 1 and cloud system 2.

Driver execution module 104 is configured to make corresponding mechanical movement according to the driver data and the human-machine environment information to perform the supporting action, so as to achieve the purpose of improving the supporting quality and also to send the behavioral and the electromechanical fatigue data of the support unit included in driver execution module 104 to local data processing module 102. Local data processing module 102 performs unit performance evaluation on the behavioral and electromechanical fatigue data, and sends the performance evaluation data of the support unit to cloud system 2;

Wherein, the support unit is used for the body support of a user with various gestures in a sleeping state, and adapts itself according to the physiological characteristics of the user and the sleep mode and real-time sleep behavior data, and also adjusts relevant parameters according to the (optimized) driver data packet, so as to improve the pressure distribution quality of the interface between the user body and support system, for the purpose of achieving follow-up support quality adjustment.

User experience evaluation measurement module 105 is configured to obtain the user's subjective attitude measurement data of sleep quality (based on the attitude metric) by using the support of the APP in the intelligent terminal, and correlate the sleep quality subjective attitude measurement data with the corresponding sleep behavior data (acquired through multi-modal/channel sensor collecting) and send the data to cloud system 2 after assigning timestamps. User experience evaluation measurement module 105 may be implemented based on the client application APP of the smart phone. Specifically, the client system application APP allows users to instantly adjust the support characteristics of the system according to their own subjective feelings (such as hardness and softness, temperature adjustment, etc.). The APP communicates with local data processing module 102 via Bluetooth and Wi-Fi based on the iOS, Android, and windows Phone systems to help the user obtain a subjectively satisfactory body support effect by changing the specific support unit parameters. The APP may also communicate with cloud system 2, which is a sleep data cloud management platform, by client system communication module 103 to obtain the user's own statistical data of sleep behavior analysis and receive the information of sleep health and health services pushed by the large system to complete system operation maintenance and services provided by the after-service system and other systems.

Human-machine conversation module 106 is configured to adjust the supporting action according to the user instruction through the support of the APP in the intelligent terminal so as to change the perceived softness of the supporting system corresponding to the user preference data, and send the user preference data to cloud system 2 through the APP after assigning a timestamp.

Further, cloud computing system 2 of the intelligent sleep system includes a cloud communication module 201, a data management module 202, a data mining module 203, a sleep quality evaluation summary analysis module 204, and a client system performance detection module 205. As a sleep data cloud management platform, cloud system 2 mainly implements three functions: management of data collected by the client node system, database data mining, and application f knowledge discovery generated by data analysis and mining.

Cloud communication module 201 is used for the wireless transmission of data between cloud system 2 and corresponding client system 1 in the cloud;

Data management module 202 is configured to, by means of cloud platform data mining, obtain a multi-dimensional user sleep behavior data set according to the widely distributed multivariate multi-channel man-machine environment information data collected by each client system 1, with an aim to support the data mining module 203 to obtain the node user sleep mode corresponding to each client system 1 and the user sleep behavior statistics corresponding to all the client systems. The user sleep behavior data set includes physical data of the time-based user sleep activity collected by client system 1 and its corresponding physiological indicator data and environmental indicator data.

Data mining module 203 is used to analyze the user sleep behavior data set by using a pattern recognition mode, in an effort to obtain the global user sleep mode of the global user and the user sleep mode of the node corresponding to each client system 1, to obtain the sleep feature knowledge of the global user and the user of the single client system, and to establish a mathematical model of a global user sleep mode and a node user sleep mode, and then generate a mode driver data packet of client system driver execution module 104 according to the global user sleep mode and the node user sleep, and send the driver data packet to client system 1. For example, based on the time sequences collected by client system 1 and the corresponding physiological indicator data and the environmental indicator data, data mining module 203 can establish a standard sleep mode after discovering the sleep mode according to the physical data of the user sleep activity so as to discover abnormal sleep mode and provide users with derived services.

Through the accumulation of a large amount of client system data, data mining module 203 allows the cloud system to discover the sleep patterns of the node users, the types and the sizes of the sleep behaviors of all the system registered users by using the methods such as cluster analysis, multi-dimensional scale analysis, regression analysis and structural equation, and to generate an optimal mathematical model of sleep pattern through the multi-dimensional analysis of sleep behavior data, user physiological indication data and environmental indicator data, so as to provide basis for the support system variable assignment determining the abnormal sleep behavior and finding the best sleep mode.

The user's sleep knowledge that is formed based on the data mining of data mining module 203 is mainly applied to the following aspects:

1—a task list for user node system maintenance and maintenance services is automatically generated, maintenance service information is pushed through the client application APP or e-mail and SMS, and delivery and maintenance after the signing of a service contract is provided.

2—a node-oriented customized system firmware is generated according to the characteristics of the client individual sleep mode, so that the improvement of the firmware layer makes the sleep experience provided by the system more in line with the needs of node users.

3—sleep experience customized data packages tailored to their sleep characteristics is pushed to the clients, such as age changes, season changes and changes in body indications (fattening, pregnancy, recuperation, paralysis, and rest in the event of critical events, such as the college entrance examination).

4—derived sleep experience services is provided: 1) whether there is any need to develop new products to help people that tend to sleep on one side achieve better sleep quality; 2) specific products for people with sleep disordered breathing (definition); 3) hypnosis TV program, hypnotic music and hypnosis service pack (music, rhythmic mattress vibration, etc.) push for hypnotic people; 4) bed room system adjustment under the non-disturbing state: activation of telephone message; generation of task lists for delivery delay; 5) media-rich wake-up products (sound, light, vibration, sealed control package); 6) sleep health counseling services (make sleep mode assessment through the server with the help of sleep research results and based on the user demographic information collected, such as age, gender, etc., and use smart phones to push persuasion information); 7) health sleep behavior correction services, etc.

5—Packet services for sleep medical/healthcare: with the growth of user data in the system, massive sleep data can provide derived data services to the medical and healthcare and related fields in the form of raw data, primary mining data and secondary mining data. The knowledge gained from sleep data mining can also transform its value in the non-sleeping field.

Sleep quality evaluation summary analysis module 204 is used to obtain the significant relationship between the sleep quality of the user at different levels and the parameters of driver execution module 104 by analyzing the user sleep behavior data set, such as the user's high-quality sleep mode parameter conditions of the node; and generate an optimized driver data packet that matches the high-quality sleep mode of each client system user based on a certain amount of data precipitation. The packet is used to drive driver execution module 104 so as to guide the user to achieve optimal sleep quality through interactive adjustment during user sleep.

Preferably, the analysis of the user sleep behavior data set specifically includes: performing a reflection layer attitude measurement on the sleep quality of the sleep activity that occurs during the valid period of the user, and the obtained measurement data will be the new data content in data management module 202; and obtaining the correlation between sleep feature knowledge and sleep quality by comparing with the existing precipitation data to generate a weighted sleep quality assessment.

Client system performance detection module 205 is used to monitor the performance of the support unit according to the performance evaluation data received from the support unit of client system 1. Specifically, client system performance detection module 205 mines (DGCM) the generated data of client system 1, so as to identify the mechatronic, hardware, and software performance of the client system and find out the harm of system fatigue caused by continuous work to the realization of client system functions, which can help cloud system 2 predict the potential failure of system or unit and generate the system maintenance service schedule. In addition, the same type of large-scale unit failure means the design defects of the system, and it will help the system's design optimization.

Customized sleep data packet 206 is used to generate a customized sleep data packet as the client system driver firmware. Client system 1 pre-processes the customized sleep data packet in local data processing module 102 and writes it into driver execution module 104 in the form of a firmware so as to provide the user with a flexibly controlled and personalized support distribution.

Preferably, sleep quality evaluation summary analysis module 204 adjusts the optimized driver data packet according to the change of the parameter values in the user sleep behavior data set over time. For example, sleep quality evaluation summary analysis module 204 is capable of adjusting the optimized driver data package by using the client system APP data. Wherein, the client system APP data includes the data generated by the users' interaction with the APP and includes the related data of the users' subjective adjustment of the support system, and it is the main way to get the user's attitude data on the supporting system.

The specific embodiments of the invention have been described above. It should be understood that the invention is not limited to the specific embodiments described above, and technicians in this field nay make various changes and modifications without departing from the spirit and scope of the appended claims, and such actions do not affect the essence of the invention.

What is claimed is:

1. A client system for an intelligent sleep system, comprising a multi-dimensional data collection module, a local data processing module, a client system communication module, and a driver execution module;
   wherein:
   the multi-dimensional data collection module is used to collect human-machine environment information associated with the sleep activity of users of the client system through a multi-mode sensor cluster, and send the human-machine environment information to the local data processing module, wherein the human-machine environment information includes the user's sleep behavior data and sleep environment data;
   the local data processing module is used to send the human-machine environment information to a cloud system connected to the client system after preprocessing, and write driver data received from the cloud system into the driver execution module;
   the client system communication module is used for wireless transmission of data between the client system and the cloud system;
   the driver execution module is used to execute a supporting action according to the driver data and the human-machine environment information.

2. The client system for an intelligent sleep system according to claim 1, further comprising one or more of the following devices:
   a user experience evaluation measurement module that is used to obtain the user's subjective attitude measurement data on sleep quality through support of an application (APP) in an intelligent terminal, and associates sleep quality subjective attitude measurement data with the corresponding sleep behavior data, and then sends the data to the cloud system after assigning a timestamp;
   a human-machine conversation module that is configured to adjust the supporting action according to the user instruction through the support of the APP in the intelligent terminal so as to change perceived softness of a supporting system corresponding to a user preference data, and sends the user preference data to the cloud system through the APP after assigning a timestamp.

3. The client system for an intelligent sleep system according to claim 1, wherein:
   the driver execution module transmits behavioral and electromechanical fatigue data of a contained support unit to the local data processing module, and the local data processing module evaluates the unit performance of the behavioral and electromechanical fatigue data and sends the performance evaluation data of the support unit to the cloud system.

4. A cloud system for an intelligent sleep system, comprising: a cloud communication module, a data management module, and a data mining module;
   wherein:
   the cloud communication module is used for wireless transmission of data between the cloud system and a client system in the cloud;
   the data management module is configured to, by means of cloud platform data mining, obtain a multi-dimensional user sleep behavior data set according to multivariate multi-channel human-machine environment information data collected by each client system, in order to support the data mining module to obtain a node user sleep mode corresponding to each client system and the user sleep behavior statistics corresponding to all the client systems;
   the data mining module is used to analyze the user sleep behavior data set by using a pattern recognition mode, in an effort to obtain a global user sleep mode of a global user and a user sleep mode of a node user corresponding to each client system, to obtain sleep feature knowledge of the global user and the user of the single client system, and to establish a mathematical model of the global user sleep mode and the node user sleep mode, and then generate a driver data packet of a driver execution module of the client system according to the global user sleep mode and the node user sleep mode, and send the driver data packet to the client system.

5. The cloud system of the intelligent sleep system according to claim 4, further comprising:
   a sleep quality evaluation summary analysis module, wherein the sleep quality evaluation summary analysis module is used to obtain significant relationship between different levels of sleep quality of the user and variables of the driver execution module by analyzing the user sleep behavior data set, and then generate an optimized driver data packet of high-quality sleep mode corresponding to users of the client system, and the optimized driver data packet is used to drive the driver execution module so as to guide the user to achieve optimal sleep quality through interactive adjustment during user sleep.

6. The cloud system of an intelligent sleep system according to claim 5, wherein analyzing the user sleep behavior data set further comprises:
   conducting a reflection layer attitude measurement on sleep quality of a sleep activity that occurs during a valid period of the user, wherein the obtained measurement data is new data content in the data management module, and correlation between the sleep feature knowledge and the sleep quality is obtained by comparison with existing precipitation data to generate a weighted sleep quality assessment.

7. The cloud system of an intelligent sleep system according to claim 5, wherein the sleep quality evaluation summary analysis module adjusts the optimized driver data packet according to a change of parameter values in the user sleep behavior data set over time.

8. The cloud system for an intelligent sleep system according to claim 4, further comprising one or more of the following devices:
   a client system performance detection module that is used to monitor the performance of a support unit according to performance evaluation data received from the support unit of the client system; and
   a customized sleep data packet generation module that is used to generate customized sleep data packet for use by a client system driver firmware.

9. The cloud system of an intelligent sleep system according to claim 4, wherein the user sleep behavior data set further comprises:

physical data of a time-sequences-based user sleep activity collected by the client system and corresponding physical indicators data and environmental indicators data.

10. An intelligent sleep system, comprising a client system and a cloud system, wherein, and the client system and the cloud system are connected wirelessly, the client system comprises a multidimensional data collection module, a local data processing module, a client system communication module, and a driver execution module, further wherein:

the multi-dimensional data acquisition module is used to collect human-machine environment information associated with the sleep activity of users of the client system through a multi-mode sensor cluster, and send the human-machine environment information to the local data processing module, wherein the human-machine environment information includes the user's sleep behavior data and sleep environment data;

the local data processing module is used to send the human-machine environment information to the cloud system connected to the client system after preprocessing, and write driver data received from the cloud system into the driver execution module;

the client system communication module is used for wireless transmission of data between the client system and the cloud system;

the driver execution module is used to execute a supporting action according to the driver data and the human-machine environment information; and wherein the cloud system comprises a cloud communication module, a data management module, and a data mining module, the cloud communication module is used for wireless transmission of data between the cloud system and the client system in the cloud;

the data management module is configured to, by means of cloud platform data mining, obtain a multi-dimensional user sleep behavior data set according to multivariate multi-channel human-machine environment information data collected by each client system, in order to support the data mining module to obtain a node user sleep mode corresponding to each client system and the user sleep behavior statistics corresponding to all the client systems;

the data mining module is used to analyze the user sleep behavior data set by using a pattern recognition mode, in an effort to obtain a global user sleep mode of a global user and a user sleep mode of a node user corresponding to each client system, to obtain sleep feature knowledge of the global user and the user of the single client system, and to establish a mathematical model of the global user sleep mode and the node user sleep mode, and then generate a driver data packet of a driver execution module of the client system according to the global user sleep mode and the node user sleep mode, and send the driver data packet to the client system.

\* \* \* \* \*

UNITED STATES PATENT AND TRADEMARK OFFICE
CERTIFICATE OF CORRECTION

| | |
|---|---|
| PATENT NO. | : 10,959,667 B2 |
| APPLICATION NO. | : 15/737035 |
| DATED | : March 30, 2021 |
| INVENTOR(S) | : Zhiyu Xin et al. |

It is certified that error appears in the above-identified patent and that said Letters Patent is hereby corrected as shown below:

In the Claims

Claim 10, Column 11, Line 16, "data acquisition module" should read -- data collection module --.

Signed and Sealed this
Tenth Day of September, 2024

Katherine Kelly Vidal
*Director of the United States Patent and Trademark Office*